(12) United States Patent
Joo

(10) Patent No.: US 9,737,210 B2
(45) Date of Patent: Aug. 22, 2017

(54) SYSTEM FOR CALCULATING CENTER OF ANTERIOR CAPSULE AND METHOD THEREOF

(71) Applicant: Catholic University Industry Academic Cooperation Foundation, Seoul (KR)

(72) Inventor: Choun-ki Joo, Seoul (KR)

(73) Assignee: the Catholic University Industry Academic Cooperation Foundation, Seoul (KR)

( * ) Notice: Subject to any disclaimer, the term of this patent is extended or adjusted under 35 U.S.C. 154(b) by 0 days.

(21) Appl. No.: 14/781,903

(22) PCT Filed: Dec. 10, 2013

(86) PCT No.: PCT/KR2013/011412
§ 371 (c)(1),
(2) Date: Oct. 1, 2015

(87) PCT Pub. No.: WO2014/163275
PCT Pub. Date: Oct. 9, 2014

(65) Prior Publication Data
US 2016/0058283 A1    Mar. 3, 2016

(30) Foreign Application Priority Data
Apr. 2, 2013    (KR) .................. 10-2013-0035549

(51) Int. Cl.
*A61B 3/14*    (2006.01)
*A61B 3/117*    (2006.01)
(Continued)

(52) U.S. Cl.
CPC .......... *A61B 3/1173* (2013.01); *A61B 3/0025* (2013.01); *A61B 3/102* (2013.01);
(Continued)

(58) Field of Classification Search
CPC ..... A61B 3/1173; A61B 3/0025; A61B 3/102; A61B 3/14; A61B 3/1216; A61B 90/361;
(Continued)

(56) References Cited

U.S. PATENT DOCUMENTS

| 2005/0110947 A1* | 5/2005 | Chaduc | A61B 3/1216 |
| | | | 351/206 |
| 2008/0319428 A1 | 12/2008 | Wiechmann et al. | |
| 2012/0274897 A1 | 11/2012 | Narasimha-Iyer | |

FOREIGN PATENT DOCUMENTS

| JP | 2008-526384 | | 7/2008 |
| JP | 2008-526384 A | * | 7/2008 |

(Continued)

*Primary Examiner* — Scott J Sugarman
*Assistant Examiner* — Mustak Choudhury
(74) *Attorney, Agent, or Firm* — Don D. Cha; Hamilton DeSanctis & Cha, LLP.

(57) ABSTRACT

The present invention provides a system and a method for performing a cataract surgery. The system of the present invention includes an optical coherence tomography apparatus, an image capturing device, and a central processing unit. The method includes imaging optical coherence tomography of a patient's eye using the optical coherence tomography apparatus, capturing the patient's optical coherence tomography with the image capturing device, generating a 3D image and coordinates of the patient's eye, and determining a central location of a pupillary margin and an iridocorneal angle using a central processing unit. The center of the anterior capsule of the human crystalline lens is then calculated by matching the iridocorneal angle to the central location of the pupillary margin.

7 Claims, 4 Drawing Sheets

(51) Int. Cl.
  *G01B 9/02*     (2006.01)
  *A61B 3/00*     (2006.01)
  *A61B 3/10*     (2006.01)

(52) U.S. Cl.
  CPC .............. *A61B 3/14* (2013.01); *G01B 9/0203* (2013.01); *G01B 9/02091* (2013.01)

(58) Field of Classification Search
  CPC .............. G01B 9/0203; A61F 9/00736; A61F 9/00838; A61F 9/009; A61F 9/00831; A61F 9/00936; A61F 9/0084; A61F 9/00825; A61F 9/00754; A61F 9/00814; A61F 9/00812; A61F 9/00834; A61F 9/008
  USPC ............. 359/206; 351/206, 246; 606/4; 623/5.15, 6.14, 6.36, 6.4, 6.44
  See application file for complete search history.

(56) References Cited

FOREIGN PATENT DOCUMENTS

| | | | | |
|---|---|---|---|---|
| JP | 2011-526165 | 10/2011 | | |
| KR | 1990-0015698 | 11/1990 | | |
| KR | 2011-0084887 | 7/2011 | | |
| WO | 2011/163524 A2 | 12/2011 | | |
| WO | WO2011-163524 A1 * | 12/2011 | ............. | A61F 9/008 |

\* cited by examiner

SYSTEM FOR CALCULATING CENTER OF ANTERIOR CAPSULE AND METHOD THEREOF

FIELD OF THE INVENTION

The present invention relates to a system for calculating the center of an anterior capsule of the crystalline lens for a cataract surgery, and a method for using the same. In particular, the present invention relates to a system for calculating the center of an anterior capsule of the crystalline lens by matching an image of a patient's eye to the data obtained by optical coherence tomography, and a method for calculating the center of an anterior capsule of the crystalline lens using the same.

BACKGROUND OF THE INVENTION

A cataract is a disease in which the crystalline lens of the eye becomes opaque, leading to a decrease in vision. In this case, when the edge of the crystalline lens becomes opaque, the cataract does not significantly affect vision, but various symptoms such as decreased visual acuity, diplopia, dazzling, and the like appear when a nuclear zone of the crystalline lens becomes opaque. The treatment for a cataract generally consists of removing an opaque crystalline lens and replacing it with an artificial intraocular lens through surgery. Such cataract surgery is one of the most widely performed surgical procedures.

Conventional cataract surgery is performed using a method which includes incising a cornea with a knife, circularly incising an anterior capsule of a crystalline lens through the incised region of the cornea, finely pulverizing the nucleus of a crystalline lens using ultrasonic waves, extracting the nucleus of the crystalline lens by suction, and inserting another intraocular lens into the region from which the nucleus of the crystalline lens was removed.

Such a cataract surgery method is similarly disclosed in Korean Unexamined Patent Application Publication No. 1990-0015698.

In such cataract surgery, the anterior capsule of the crystalline lens is preferably incised in the form of a circle or as close as possible because of the following reasons.

First, when the anterior capsule of the crystalline lens is removed in one piece, a situation in which surgery in a future operative stage is hindered because the presence of the anterior capsule of the crystalline lens may be prevented.

Second, lens luxation may be prevented because a force applied to the anterior capsule of the crystalline lens during the surgery may be uniformly spread to disperse a force applied to a ligament of the crystalline lens.

Third, the eye may be in a stable close system when the anterior capsule of the crystalline lens is incised in a circle, thereby preventing damage to a posterior capsule.

Fourth, when intracapsular manipulations (nuclear segregation, nuclear fragmentation, intraocular lens manipulating, etc.) are performed during the surgery, surgical complications may be reduced due to high physical stability.

Fifth, the contraction and opacification of the capsule after the surgery may be prevented, thereby preventing blurred vision which may recur after the surgery.

Also, in addition to the incision shape upon incision of the anterior capsule, an incision size is an important factor determining the success or failure of the surgery. Generally, the size of an incised section is preferably slightly smaller than that of an optical zone of an intraocular lens. When the size of the incised section is larger than that of the optical zone of the intraocular lens, the lens luxation, iris incarceration or dislocation, etc. may occur, leading to blurred vision, and a reoperation should be performed when the blurred vision is severe.

On the other hand, when the size of the incised section is too small, the contraction of the sac may occur to conceal the visual axis, thereby causing blurred vision, the opacification of the anterior capsule of the crystalline lens and posterior capsule may be caused, thereby requiring an additional surgical operation, and the dislocation of the intraocular lens may be caused, thereby deteriorating the quality of vision after the surgery. Korean Unexamined Patent Application Publication No. 2011-0084887 discloses a device for capsulorhexis.

In recent years, the importance of incision of the anterior capsule of the crystalline lens with a perfect circle and proper size has increased with an increase in the use of multifocal intraocular lenses for presbyopic correction, and intraocular lenses for correction of astigmatism. In the case of these intraocular lenses, postoperative complications, such as lens dislocation, posterior capsular opacity, and the like have a larger effect on vision acuity than the unifocal intraocular lenses, and additional manipulations themselves performed to address occurring complications may cause degradation in the performance of the intraocular lenses.

Meanwhile, another factor determining the success or failure of the surgery is an incision location of the anterior capsule. When the incision location of the anterior capsule of the crystalline lens deviates from the center of the crystalline lens, the dislocation and slope of the crystalline lens, and the like may occur, and postoperative posterior capsular opacity may easily occur, resulting in degraded surgical efficiency.

Generally, experienced surgeons incise an anterior capsule of the crystalline lens based on the size of a patient's cornea, and the size of a dilated pupil. However, since individual patients have different cornea sizes and the dilated pupils are not uniform in size, the final size and location may not be fixed.

Since the incision shape and location of the anterior capsule of the crystalline lens fully depend on the surgeons' experience and techniques, it is very difficult to incise the anterior capsule of the crystalline lens in a perfect circle and a proper location. Also, when the incision size and shape of the anterior capsule of the crystalline lens is not perfect, an additional surgical procedure should be performed to adjust the size of a capsule of the crystalline lens after insertion of the intraocular lens, resulting in wasted time and effort.

Since the incision of the anterior capsule of the crystalline lens itself is a very elaborate surgical procedure as described above, a method capable of guiding an exact size and location during the incision of the anterior capsule of the crystalline lens is required.

SUMMARY OF THE INVENTION

The present invention is designed to solve the problems of the prior art, and therefore it is an object of the present invention to provide a system for calculating the center of an anterior capsule of the crystalline lens which is capable of determining a location of the anterior capsule of the crystalline lens upon cataract surgery, exactly calculating the center of the anterior capsule of the crystalline lens and presenting the center of the anterior capsule of the crystalline lens to a surgeon, and a method for calculating the center of an anterior capsule of the crystalline lens using the same.

The objects of the present invention are not limited thereto, and other objects of the present invention which are not disclosed herein will become more apparent to those of ordinary skill in the art by describing in detail exemplary embodiments thereof.

According to an aspect of the present invention, there is provided a method for calculating the center of an anterior capsule, which includes the steps of imaging a patient's eyeball with optical coherence tomography, generating a 3-dimensional (3D) image and coordinates based on the data obtained by the optical coherence tomography, capturing the patient's eyeball to produce an eyeball image, and calculating the center of an anterior capsule of the crystalline lens of the patient by matching the 3D image and coordinates to the eyeball image.

In this case, the calculating of the center of the anterior capsule of the crystalline lens may include the operations of calculating a central location of a pupillary margin, calculating an iridocorneal angle, and calculating the center of the anterior capsule of the crystalline lens by matching the iridocorneal angle to the central location of the pupillary margin.

Also, the calculating of the iridocorneal angle may be performed by calculating a contact point formed by extending a bisecting point of the iridocorneal angle, and the calculating of the center of the anterior capsule of the crystalline lens may be performed by calculating an extension line extending from the contact point to the center of the pupillary margin.

In addition, after the calculating of the center of the anterior capsule, the method may further include the step of displaying the calculated center of the anterior capsule of the crystalline lens to a surgeon.

Additionally, the displaying of the center of the anterior capsule of the crystalline lens may be performed by displaying the center of the anterior capsule of the crystalline lens to the surgeon through an optical device used during surgical operations.

According to another aspect of the present invention, there is provided a system for calculating the center of an anterior capsule. Here, the system includes an optical coherence tomography apparatus configured to image a patient's eyeball with optical coherence tomography, an image capturing device configured to capture the patient's eyeball to produce an eyeball image, and a central processing unit configured to generate a 3D image and coordinates based on the data obtained by the optical coherence tomography apparatus and calculate the center of an anterior capsule of the crystalline lens by matching the 3D image and coordinates to the eyeball image obtained by the image capturing device.

In this case, the system may further include an optical device configured to display the center of the anterior capsule of the crystalline lens calculated by the central processing unit to a surgeon.

Also, the central processing unit may include a first operation unit configured to generate the 3D image and coordinates based on the data obtained by the optical coherence tomography apparatus, and a second operation unit configured to calculate the center of the anterior capsule of the crystalline lens by matching the 3D image and coordinates to the eyeball image obtained by the image photographing device.

The system for calculating the center of an anterior capsule, and the method for calculating the center of an anterior capsule of the crystalline lens using the same according to the exemplary embodiments of the present invention have effects of allowing a surgeon to objectively recognize where the center of a crystalline lens is through an optical device such as an operating microscope during cataract surgery, and performing a surgical procedure more effectively when an anterior capsule of the crystalline lens is incised based on the data obtained in this way.

Also, the system and the method according to the exemplary embodiments of the present invention have effects of prolonging the effects of surgical and promoting patient safety.

The objects of the present invention are not limited thereto, and other objects of the present invention which are not disclosed herein will become more apparent to those of ordinary skill in the art by describing in detail exemplary embodiments thereof.

DETAILED DESCRIPTION OF THE INVENTION

Hereinafter, a system for calculating the center of an anterior capsule of the crystalline lens according to exemplary embodiments of the present invention, and a method for calculating the center of an anterior capsule of the crystalline lens using the same will be described in detail with reference to the accompanying drawings.

Figure 1:
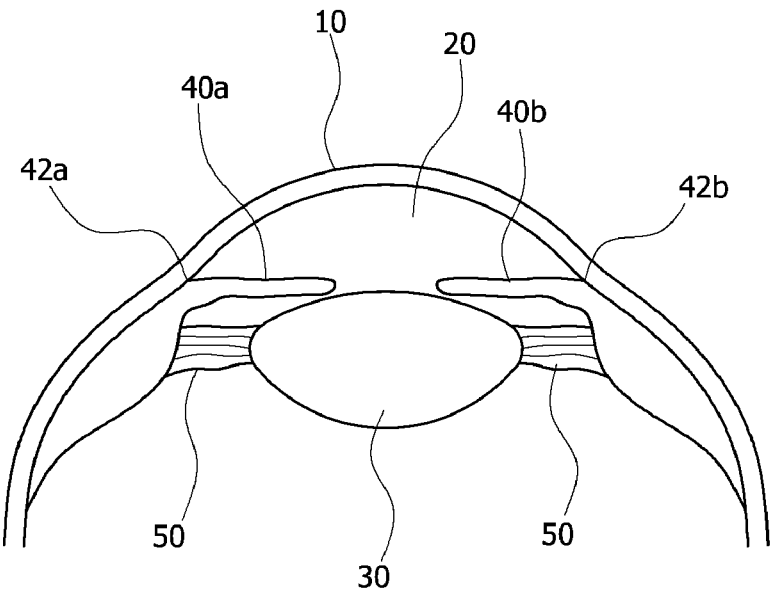
FIG. 1 is a cross-sectional view showing a structure of an eyeball.

FIG. 1 shows a structure of an eye.

A crystalline lens 30 is present inside an eye. Here, the crystalline lens 30 is connected to a ciliary body through a ciliary ligament 50 at an equator. Also, iris portions 40a and 40b are positioned at both frontal sides of the crystalline lens, and angles formed between a cornea 10 and iris edges 42a and 42b are referred to as iridocorneal angles. Also, an anterior capsule of the crystalline lens 20 of the crystalline lens is present between the crystalline lens 30 and the cornea 10.

That is, the anterior capsule of the crystalline lens 20 needs to be incised to extract the nucleus of the crystalline lens and insert an intraocular lens during cataract surgery. In this case, the anterior capsule of the crystalline lens 20 should be incised in a circle with a proper size, as described above in the technical field of the present invention.

Also, although it is important to incise a central region of the anterior capsule of the crystalline lens 20, there is difficulty in finding the central region of the anterior capsule of the crystalline lens 20 exactly since the iridocorneal angles, and the shapes of a pupillary margin that is an outer circumferential surface of a pupil are different according to patients.

Therefore, a method of calculating the center of the anterior capsule of the crystalline lens 20, and a system used in the method are provided in the present invention.

Figure 2:
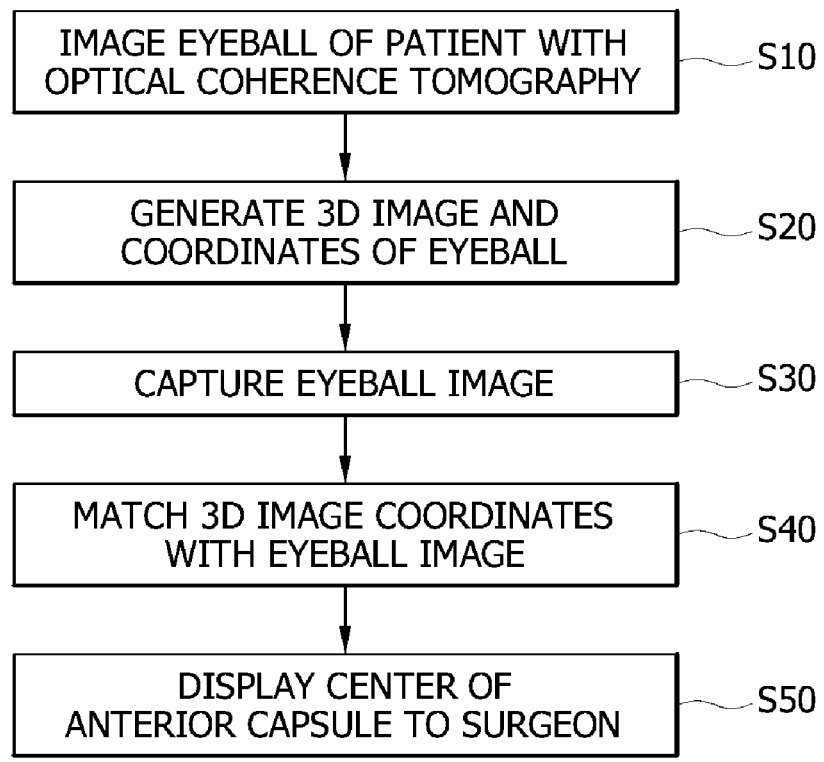
FIG. 2 is a flowchart illustrating respective steps of a method for calculating the center of an anterior capsule of the crystalline lens according to one exemplary embodiment of the present invention.

FIG. 2 is a flowchart illustrating respective steps of the method for calculating the center of an anterior capsule of the crystalline lens according to one exemplary embodiment of the present invention.

Figure 3:
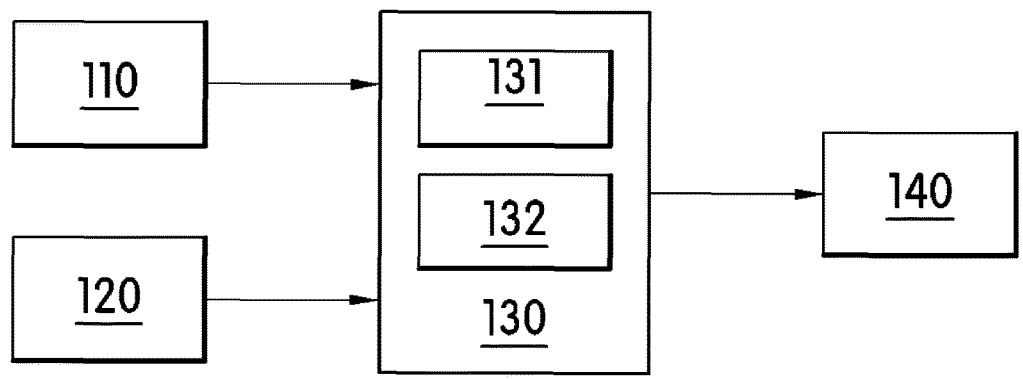
FIG. 3 is a block diagram of a system for calculating the center of an anterior capsule of the crystalline lens according to one exemplary embodiment of the present invention.

FIG. 3 is a block diagram of a system for calculating the center of an anterior capsule of the human crystalline lens according to one exemplary embodiment of the present invention.

As shown in FIG. 2, the method for calculating the center of an anterior capsule of the crystalline lens according to one exemplary embodiment of the present invention includes the steps of imaging a patient's eyeball with optical coherence tomography (S10), generating a 3D image and coordinates based on the data obtained in the imaging of the patient's eyeball with the optical coherence tomography (S10) (S20), capturing the patient's eyeball to produce an eyeball image (S30), and calculating the center of an anterior capsule of the crystalline lens of the patient by matching the 3D image and coordinates to the eyeball image (S40). After the calculating of the center of the anterior capsule, the method may further include displaying the calculated center of the anterior capsule of the crystalline lens to a surgeon (S50).

Hereinafter, the respective steps will be described in detail.

First, the imaging of the patient's eyeball with the optical coherence tomography (S10) is a step of obtaining the data on the patient's eyeball through an optical coherence tomography apparatus (OCT) 110.

After the imaging of the patient's eyeball with the optical coherence tomography (S10), the generating of the 3D image and coordinates based on the obtained data (S20) may be performed. In this step, an operation of setting coordinates for each of points of the 3D image according to an algorithm set through a central processing unit 130 is performed.

Next, the capturing of the patient's eyeball to produce the eyeball image (S30) is performed. In this step, the eyeball image of the patient is obtained through an image capturing device 120 such as a camera.

Then, the calculating of the center of the anterior capsule of the crystalline lens of the patient (S40) is performed. In this step, the center of the anterior capsule of the crystalline lens is calculated by matching the 3D image and coordinates obtained in the imaging of the patient's eyeball with the optical coherence tomography (S10) to the eyeball image obtained in the capturing of the patient's eyeball to produce the eyeball image (S30).

In this case, the above-described central processing unit 130 is used to calculate the center of the anterior capsule. The central processing unit 130 used in this step may be the same device as the central processing unit 130 used in the generating of the 3D image and coordinates (S20), or may be installed as a separate device.

Also, the central processing unit 130 may include a first operation unit 131 configured to generate the 3D image and coordinates based on the data obtained by the optical coherence tomography apparatus 110, and a second operation unit 132 configured to calculate the center of the anterior capsule of the crystalline lens by matching the 3D image and coordinates to the eyeball image obtained by the image capturing device 120.

Hereinafter, the calculating of the center of the anterior capsule of the crystalline lens will be described in further detail.

Figure 4:
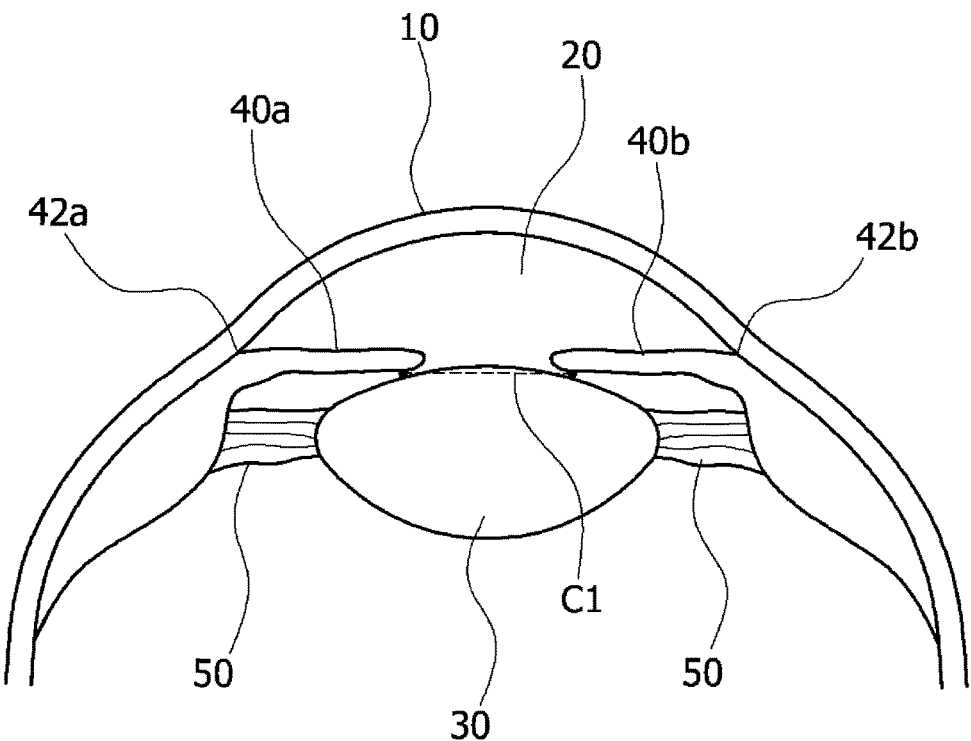
FIG. 4 is a cross-sectional view showing an operation of calculating the center of a pupillary margin in the method for calculating the center of an anterior capsule of the crystalline lens according to one exemplary embodiment of the present invention.

FIG. 4 is a cross-sectional view showing an operation of calculating the center of a pupillary margin in the method for calculating the center of an anterior capsule of the crystalline lens according to one exemplary embodiment of the present invention.

As shown in FIG. 4, the central processing unit 130 serves to calculate the shape of the pupillary margin based on the 3D data. The circular pupillary margin may be indicated by a first extension line C1 extending from inner portions of the iris portions 40a and 40b based on a cross section of the eyeball for the sake of convenience.

Figure 5:
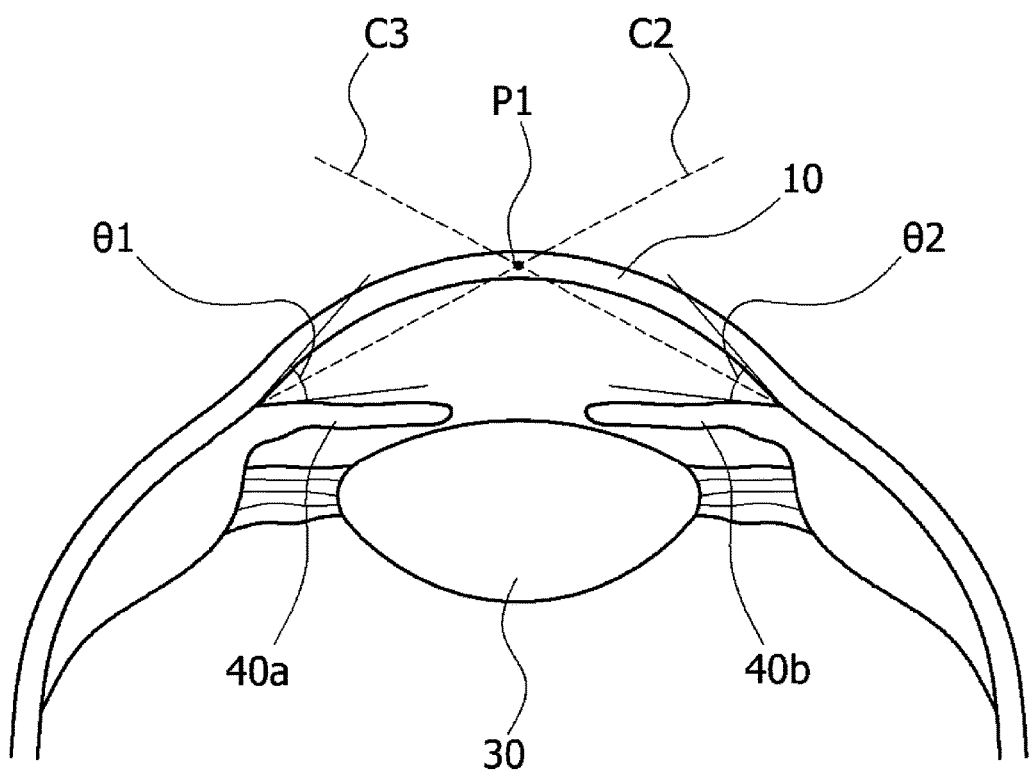
FIG. 5 is a cross-sectional view showing an operation of calculating a contact point of an iridocorneal angle in the method for calculating the center of an anterior capsule of the crystalline lens according to one exemplary embodiment of the present invention.

FIG. 5 is a cross-sectional view showing an operation of calculating a contact point of an iridocorneal angle in the method for calculating the center of an anterior capsule of the crystalline lens according to one exemplary embodiment of the present invention.

As shown in FIG. 5, iridocorneal angles θ1 and θ2 formed between the iris edges and the cornea 10 may extend in a circle around the eyeball. In this exemplary embodiment, a contact point P1 formed at an intersection of a second extension line C2 and a third extension line C3 which bisect the iridocorneal angles θ1 and θ2, respectively, based on the cross section of the eyeball, is obtained in the calculating of the iridocorneal angle.

Figure 6:
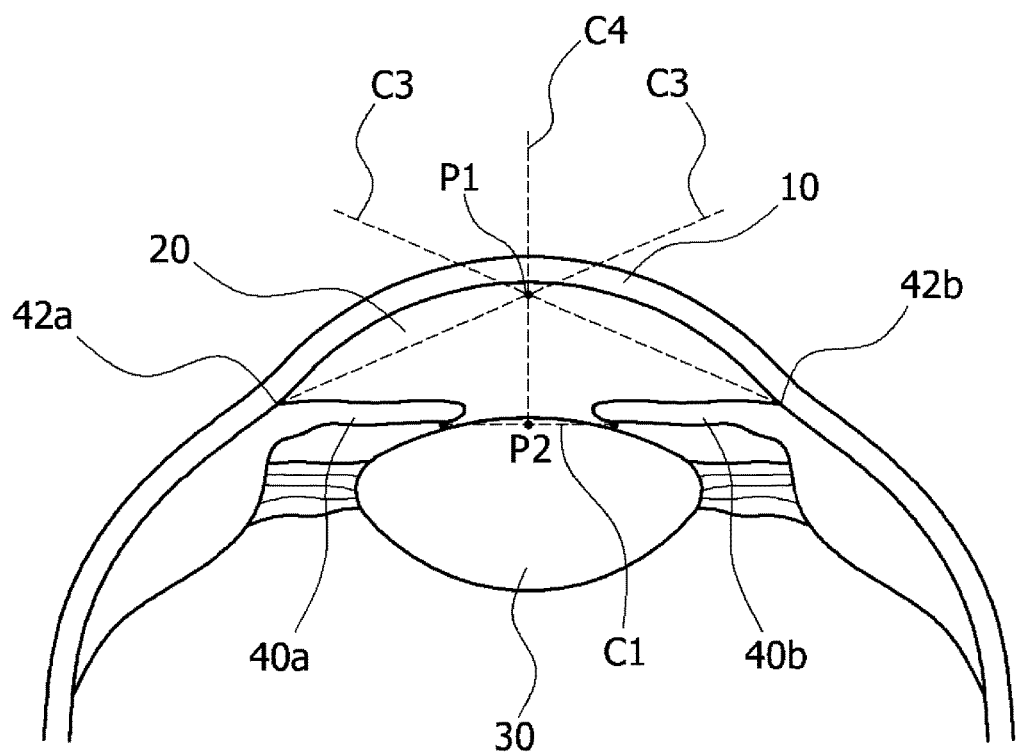
FIG. 6 is a cross-sectional view showing an operation of extending a contact point of an iridocorneal angle to a central location of a pupillary margin to calculate the center of the anterior capsule of the human crystalline lens in the method for calculating the center of an anterior capsule of the human crystalline lens according to one exemplary embodiment of the present invention.

FIG. 6 is a cross-sectional view showing an operation of extending a contact point P1 of an iridocorneal angle to a central location P2 of a pupillary margin to calculate the center of the anterior capsule of the crystalline lens in the method for calculating the center of an anterior capsule of the crystalline lens according to one exemplary embodiment of the present invention.

In this operation, a fourth extension line C4 connecting a contact point P1 of the iridocorneal angle and the central location P2 of the pupillary margin calculated respectively in the above-described operations may be extended. Here, a fourth extension line C4 represents the center of the anterior capsule. That is, a surgeon may perform a stable surgical procedure by incising the center of the anterior capsule of the crystalline lens along the fourth extension line C4.

Figure 7:
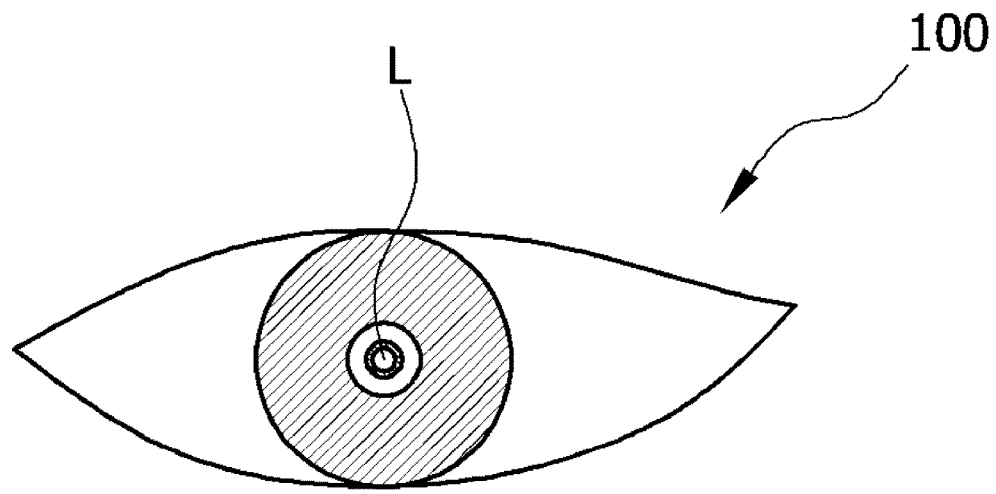
FIG. 7 is a diagram showing the center of the anterior capsule of the crystalline lens displayed to a surgeon through an optical device used in surgical procedures in the method for calculating the center of an anterior capsule of the crystalline lens according to one exemplary embodiment of the present invention.

FIG. 7 is a diagram showing the center of the anterior capsule of the crystalline lens displayed to a surgeon through an optical device used during surgical operations in the method for calculating the center of an anterior capsule of the crystalline lens according to one exemplary embodiment of the present invention.

In this step, the center of the anterior capsule of the crystalline lens calculated by the central processing unit 130 in the above-described steps is displayed to a surgeon during surgical procedures, which may be achieved using various methods.

According to this exemplary embodiment, the displaying of the center of the anterior capsule of the crystalline lens may be performed by displaying the center of the anterior capsule of the crystalline lens to the surgeon through the optical device 140 used during cataract surgical operations. In this case, the optical device 140 may be used to directly display a central point L of the anterior capsule of the crystalline lens onto an eyeball 100 of a patient, or may be directly mounted in a microscope used by the surgeon to display the central point of the anterior capsule of the crystalline lens on a lens.

Also, the center of the anterior capsule of the crystalline lens may be displayed to the surgeon using various methods, but the present invention is not limited thereto.

The exemplary embodiments and the accompanying drawings provided and shown herein are merely examples which exemplarily describe the scope of the present invention. Therefore, it is apparent that the scope of the present invention is not limited to the exemplary embodiments thereof since the exemplary embodiments disclosed herein are intended to describe the scope of the present invention, but not intended to limit the scope of the present invention. Accordingly, it will be apparent to those skilled in the art that various changes and modifications can be made to the above-described exemplary embodiments of the present invention without departing from the scope of the present invention. Thus, it should be understood that the present invention covers all such changes and modifications provided they come within the scope of the appended claims and their equivalents.

The invention claimed is:

1. A method for calculating the center of an anterior capsule of the crystalline lens of a patient for a cataract surgery, comprising the steps of:
    imaging a patient's eye with optical coherence tomography;
    generating a 3-dimensional (3D) image and coordinates based on the data obtained by the optical coherence tomography;
    capturing an image of the patient's eye; and
    calculating the center of an anterior capsule of the crystalline lens of the patient by matching the 3D image and coordinates to the image of the patient's eye, wherein the calculating of the center of the anterior capsule of the crystalline lens comprises the steps of:
    calculating a central location of a pupillary margin;
    calculating an iridocorneal angle; and
    calculating the center of the anterior capsule of the crystalline lens by matching the iridocorneal angle to the central location of the pupillary margin.

2. The method of claim 1, wherein said step of calculating the iridocorneal angle is performed by calculating a contact point formed by extending a bisecting point of the iridocorneal angle, and said step of calculating the center of the anterior capsule of the crystalline lens is performed by calculating an extension line extending from contact point to the center of the pupillary margin.

3. The method of claim 1, further comprising the step of
    displaying the calculated center of the anterior capsule of the crystalline lens to a surgeon.

4. The method of claim 3, wherein the calculated center of the anterior capsule of the crystalline lens is displayed to the surgeon through an optical device used during cataract surgery.

5. A system for calculating the center of an anterior capsule of the crystalline lens of a patient during a cataract surgery, the system comprising:
    an optical coherence tomography apparatus configured to image a patient's eye with optical coherence tomography;
    an image capturing device configured to capture an image of the patient's eye; and
    a central processing unit configured to generate a 3D image and coordinates based on the data obtained by the optical coherence tomography apparatus and calculate the center of an anterior capsule of the crystalline lens by matching the 3D image and coordinates to the image of the patient's eye obtained by the image capturing device,
    wherein the central processing unit calculates a central location of a pupillary margin and an iridocorneal angle, and wherein the center of the anterior capsule of the crystalline lens is calculated by matching the iridocorneal angle to the central location of the pupillary margin.

6. The system of claim 5, further comprising an optical device configured to display the center of the anterior capsule of the crystalline lens calculated by the central processing unit to a surgeon.

7. The system of claim 5, wherein the central processing unit comprises:
    a first operation unit configured to generate the 3D image and coordinates based on the data obtained by the optical coherence tomography apparatus; and
    a second operation unit configured to calculate the center of the anterior capsule of the crystalline lens by matching the 3D image and coordinates to the image of the patient's eye obtained by the image capturing device.

* * * * *